United States Patent [19]

Smith, Jr. et al.

[11] 4,411,694

[45] Oct. 25, 1983

[54] EMULSIFIABLE CONCENTRATES OF 2-CHLORO-N-ISOPROPYL-2',3'-DIMETHYLACETANILIDE WITH IMPROVED RESISTANCE TO CRYSTALLIZATION AND PROCESS FOR PREPARING THE SAME

[75] Inventors: Frank H. Smith, Jr., Titusville, N.J.; Pradip K. Mookerjee, Martinez, Calif.

[73] Assignee: American Cyanamid Company, Stamford, Conn.

[21] Appl. No.: 324,221

[22] Filed: Nov. 23, 1981

Related U.S. Application Data

[63] Continuation-in-part of Ser. No. 156,010, Jun. 3, 1980, abandoned.

[51] Int. Cl.$^3$ ............................................. A01N 57/00
[52] U.S. Cl. ......................................... 71/118; 71/86; 71/122; 71/DIG. 1
[58] Field of Search .................... 71/118, DIG. 1, 122

[56] References Cited

U.S. PATENT DOCUMENTS

| | | | |
|---|---|---|---|
| 3,421,882 | 1/1969 | Ordas | 71/111 |
| 3,792,996 | 2/1974 | Barron et al. | 71/115 |
| 3,986,862 | 10/1976 | Armstrong | 71/118 |
| 4,021,483 | 5/1977 | Lutz et al. | 564/305 |
| 4,163,662 | 8/1979 | Baker, Jr. | 71/118 |
| 4,174,960 | 11/1979 | Hendriksen | 71/DIG. 1 |
| 4,224,049 | 9/1980 | Devisetty et al. | 71/86 |
| 4,313,847 | 2/1982 | Chasin et al. | 71/118 |
| 4,349,379 | 9/1982 | Horide et al. | 71/DIG. 1 |

OTHER PUBLICATIONS

McCutcheon, "Detergents and Emulsifiers" (1976), McCutcheon Div. Pub. Co. pp. 48, 49, 52, 53, 138 & 139 (1976).

*Primary Examiner*—Glennon H. Hollrah
*Attorney, Agent, or Firm*—William H. Calnan

[57] ABSTRACT

There are provided herbicidal emulsifiable concentrates which comprise an homogeneous mixture of 2-chloro-N-isopropyl-2',3'-dimethylacetanilide with phenol, surfactants and a solvent, wherein said concentrates are characterized by improved resistance to recrystallization of the above herbicide from same.

4 Claims, No Drawings

EMULSIFIABLE CONCENTRATES OF 2-CHLORO-N-ISOPROPYL-2',3'-DIMETHYLACETANILIDE WITH IMPROVED RESISTANCE TO CRYSTALLIZATION AND PROCESS FOR PREPARING THE SAME

This application is a continuation-in-part of application Ser. No. 156,010, filed June 3, 1980, now abandoned.

The present invention is directed to a herbicidal composition. More particularly, the invention relates to a herbicidal composition which comprises an emulsifiable concentrate of 2-chloro-N-isopropyl-2',3'-dimethylacetanilide with improved resistance to crystallization. Still more particularly, the invention is concerned with an improved herbicidal composition resistant to crystallization by incorporating into said emulsifiable composition, a phenol in amounts sufficient to depress the crystallization point of said herbicide.

The herbicide, 2-chloro-N-isopropyl-2',3'-dimethylacetanilide, and a method of use have been disclosed in U.S. Pat. No. 4,021,483, herein incorporated by reference. This herbicide when applied preemergence, is highly selective for the control of undesired grass plants in the presence of crops such as corn, cotton and rice. Unfortunately, however, emulsifiable concentrates of the above herbicide prepared by known methods and employing conventional solvents exhibit poor resistance to crystallization at low temperatures. Thus, for instance, an emulsifiable concentrate containing approximately 479 g/l (4 lb/gal) of the above active ingredient will deposit large crystals of same within one week of storage at 4.4° C. (40° F.). Since these crystals generally remain undissolved when emulsifiable concentrates of this type are warmed to temperatures encountered in agricultural use, the compositions are rendered unsuitable for their intended use. Accordingly, the presence of crystals in an emulsifiable concentrate is unacceptable because such crystals or other solid matter could conceivably incapacitate and/or possibly damage devices used in agriculture for the application of these compositions even after they have been diluted with water or some other suitable inert solvent to the concentration desired. Additionally, crystallization or precipitation of the active ingredient will lower its concentration in said emulsifiable concentrates to levels at which directions for use are invalidated.

It has now been found that by the novel composition and method of the present invention, the above difficulties can be alleviated and satisfactory emulsifiable concentrates may be prepared. Thus, the admixture of 2-chloro-N-isopropyl-2',3'-dimethylacetanilide with a predetermined amount of phenol provides a liquid composite which on blending with suitable surfactants and solvents yields emulsifiable concentrates with improved resistance to crystallization and/or precipitation at low temperatures. It is noted, for instance, that an emulsion containing approximately 659 g/l (5.5 lb/gal) of active ingredient and 18.8% by weight of phenol, a molar ratio of active ingredient to phenol of 1:0.8, can be stored at −6.7° C. (20° F.) with no observable crystallization. Without the phenol, partial crystallization of the toxicant will occur upon batch cooling from 45° C. to 25° C.

In general, the emulsifiable concentrate composition of the present invention comprises in admixture from about 50% by weight to about 70% by weight and, preferably, from 64% to 66% by weight of 2-chloro-N-isopropyl-2',3'-dimethylacetanilide (usually from 90% to 97% purity), from about 15% by weight to about 30% by weight and preferably 18.8% to 27% by weight of phenol, the preferred molar ratio of active ingredient to phenol being from about 1:0.8 to 1:1.1, and the most preferred molar ratio of active ingredient to phenol being from about 1:0.85 to 1:1.05, from about 2% by weight to about 15% by weight and, preferably, from 3% to 13% by weight of a surfactant or a blend of a pair of surfactants used in a 1:1 to 4:1 weight ratio, wherein said surfactants are selected from the group consisting of ammonium alkylaryl ether sulfate, mixtures of dodecylbenzene sulfonate and ethoxylated nonylphenol, blends of alkylphenoxy polyethoxy ethanols and organic sulfonates, organic phosphate ester free acids, blends of alkylaryl sulfonates and polyoxyethylene alkyl aryl ethers, and the resultant composition is then totaled to 100% with an inert aromatic solvent. Exemplary inert aromatic solvents include toluene, xylene, monochlorobenzene, a highly aromatic, high solvency naphtha with a high boiling range and slow evaporation rate, have the following specification:

| | |
|---|---|
| Specific gravity at 15.56/15.56° C. | 0.986 |
| wt in g/l at 15.56° C. (lb/gal) | 983.8; (8.21) |
| boiling point range °C. | 212–272 |
| aromatics in Vol % | 99 |
| mixed aniline point °C. | 12 |
| Flash point, COC; °C. | 34.4 |
| Viscosity SSU at 37.8° C. | 37 |
| and another but more preferred aromatic solvent, having the following specification: | |
| Specific gravity at 15.56/15.56° C. | 0.853–0.875 |
| Flash point TCC min °C. | 37.8 |
| Kauri - Butanol value, min. | 92 |
| Aromatics Vol %, min | 95 |
| boiling point range °C. | 143–171 |

| Composition | % |
|---|---|
| non-aromatics | 4.40 |
| ethylbenzene | 0.26 |
| 1,2-xylene | 32.29 |
| 1,3-xylene | 1.25 |
| 1,4-xylene | 0.75 |
| 1,2-methyl-ethylbenzene | 5.05 |
| 1,3-methyl-ethylbenzene | 4.94 |
| 1,4-methyl-ethylbenzene | 17.75 |
| 1,2,3-trimethylbenzene | 3.62 |
| 1,2,4-trimethylbenzene | 22.45 |
| 1,3,5-trimethylbenzene | 6.53 |
| $C_{10}$ aromatics, and heavier | 0.75 |
| | 100.00 |

Advantageously, an emulsifiable concentrate composition of the present invention can be prepared by meltint 66% by weight of 2-chloro-N-isopropyl-2',3'-dimethylacetanilide (of 93% purity) and maintaining the melt at 65° C. to 70° C., while 23.5% by weight of phenol is added with stirring. After a homogeneous melt is obtained, a mixture of two surfactants is added comprising: 6.2% by weight of the first surfactant which is a mixture of dodecylbenzene sulfonate and ethoxylated nonylphenol, and 1.6% by weight of the second surfactant which is a mixture of mono and diesters of orthophosphoric acid represented by the following structures:

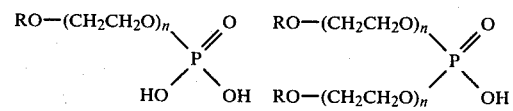

wherein R is $C_8$-$C_{20}$ alkylphenyl and n is an integer of 6 to 8. Next, the melt is cooled to 30° C. and there is added thereto an inert aromatic solvent having the following average composition and physical characteristics:

| Composition | % |
| --- | --- |
| non-aromatics | 4.40 |
| ethylbenzene | 0.26 |
| 1,2-xylene | 32.29 |
| 1,3-xylene | 1.25 |
| 1,4-xylene | 0.75 |
| 1,2-methyl-ethylbenzene | 5.05 |
| 1,3-methyl-ethylbenzene | 4.93 |
| 1,4-methyl-ethylbenzene | 17.75 |
| 1,2,3-trimethylbenzene | 3.62 |
| 1,2,4-trimethylbenzene | 22.45 |
| 1,3,5-trimethylbenzene | 6.50 |
| $C_{10}$ aromatics, and heavier | 0.75 |
| | 100.00 |
| Specific gravity at 15.56/15.56 | 0.853–0.875 |
| flash point TCC min. °C. | 37.8 |
| Kauri - Butanol value, min. | 92 |
| Aromatics, Vol %, min. | 95 |
| boiling point range °C. | 143–171 | in amounts sufficient to adjust the composition to 100%, usually about 2.7%, by weight, based on the overall composition. The emulsifiable concentrate thus obtained yields stable emulsions and does not deposit crystals at or above −1° C. (30° F.).

Alternatively, the 2-chloro-N-isopropyl-2′,3′-dimethylacetanilide herbicide (mp 56° C.) and phenol (mp 43° C.) are melted separately. The melts are then mixed resulting in the formation of an eutectic mixture. Surfactants and solvent are added after cooling to 25°–30° C.

In another alternative manner, the compositions can also be prepared by blending together the components in particulate form at room temperature until liquefaction is complete, followed by the addition of hereinabove identified emulsifiers and solvents. The use of cresylic acid, a mixture of o, m and p-cresols, especially obviates the need for externally applied heat as it is a heat and induces eutectic formation very readily.

As stated above, the emulsifiable concentrates of the novel composition of the present invention are stable and resist crystallization at relatively low temperatures. Thus, these compositions may be prepared and stored well in advance of intended use. However, the emulsifiable concentrates may be diluted with water or some other inert solvent, as desired, to obtain dilute sprays for the delivery of the active component required.

The following, non-limiting examples serve to further illustrate the present invention.

EXAMPLE 1

Preparation of emulsifiable concentrates containing 2-chloro-N-isopropyl-2′,3′-dimethylacetanilide and phenol The herbicide, 2-chloro-N-isopropyl-2′,3′-dimethylacetanilide, is melted and the melt maintained at 65° to 70° C. while a predetermined amount of phenol is added with stirring. Heating and stirring is continued until the mixture becomes homogeneous. The selected surfactants are then added and agitation continues until the melt becomes homogeneous. Next, the mixture is cooled to 30° C., the requisite amount of solvent added and agitation continued until a solution is obtained. Finally, the solution is clarified by filtration.

The thus prepared formulations are then evaluated as follows:

1. Spontaneity of emulsification, and stability of the emulsions formed.

A 5 ml sample of the formulation is added to 95 ml of tap water contained in a 100 ml graduated cylinder from a pipette, the tip of which is held approximately 5 cm above the surface of the water.

Bloom is visually estimated as the approximate percentage (by volume) of formulation that spontaneously emulsifies during addition.

Next, the cylinder is slowly inverted 30 times to obtain an emulsion, and the cylinder allowed to stand for 30 minutes. At the end of 30 minutes, the degree of phase separation which is indicative of the stability of the emulsion is determined in milliliters.

2. Crystallization

Samples of the formulation are stored at −6.7° C. (20° F.), −3.9° C. (25° F.) and −1.1° C. (30° F.). After having been stored at the above temperatures for 24 hours, seed crystals are introduced into the samples, and observations are made after 7 days. Samples showing signs of crystallization of −1.1° C. (30° F.) are allowed to stand at room temperature for 24 hours to see if the crystals would redissolve spontaneously. The samples are rated according to the appropriate rating systems appended to Tables Ia and Ib, hereinbelow set forth. The compositions of the various formulations is also given in said tables.

Abbreviations

Surfactants a = ammonium alkylaryl ether sulfate sp. grav 1.055; anionic activity 59%.
b = experimental emulsifier of undisclosed composition.
c = experimental emulsifier of undisclosed composition.
d = mixture of dodecylbenzene sulfonate and ethoxylated nonylphenol
e = blend of alkylphenoxy polyethoxy ethanols and organic sulfonates
f = organic phosphate ester free acid.
g = organic phosphate ester free acid.
h = blend of alkylaryl sulfonate and polyoxyethylene alkyl aryl ether
i = blend of alkylaryl sulfonate and polyoxyethylene alkyl aryl ether
j = experimental emulsifier blends of undisclosed composition Solvents MCB = monochlorobenzene
3-NOX = 3-nitro-o-xylene
n. phen. = nonyl phenol
m. ol = methyl oleate
$N_1$ = highly aromatic solvent, having the following specification:

| | |
| --- | --- |
| Specific gravity at 15.56/15.56° C. | 0.986 |
| wt in g/l (lb/gal) at 15.56° C. | 983.8 (8.21) |
| boiling point range °C. | 212–272 |
| aromatic in Vol % | 99 |
| mixed aniline point °C. | 12 |
| Flash point, COC °C. | 34.4 |
| Viscosity SSU at 37.8° C. | 37 |

$N_2$ = highly aromatic solvent having the following specification and composition:

| | |
| --- | --- |
| Specific gravity at 15.56/15.56° C. | 0.853–0.875 |
| flash point TCC; min. °C. | 37.8 |
| Kauri - Butanol value; min. | 92 |

-continued

| | |
|---|---|
| Aromatics in Vol %; min. | 95 |
| boiling point range °C. | 143–171 |

| Composition | % |
|---|---|
| non-aromatics | 4.40 |
| ethylbenzene | 0.26 |
| 1,2-xylene | 32.29 |
| 1,3-xylene | 1.25 |
| 1,4-xylene | 0.75 |
| 1,3-methyl-ethylbenzene | 5.05 |
| 1,3-methyl-ethylbenzene | 4.93 |
| 1,4-methyl-ethylbenzene | 17.75 |
| 1,2,3-trimethylbenzene | 3.62 |
| 1,2,4-trimethylbenzene | 22.45 |
| 1,3,5-trimethylbenzene | 6.50 |
| $C_{10}$ aromatics, and heavier | 0.75 |
| | 100.00 |

$N_3$ = highly aromatic solvent, similar to $N_1$ and $N_2$, hereinabove.

Surfactants f and g above are mixtures of mono- and diesters of orthophosphoric acid represented by the following structures:

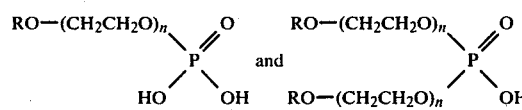

wherein R is $C_8$–$C_{20}$ alkyl or alkylphenyl and n is the number of moles of ethylene oxide condensed with hydrophobe R-OH, and represents an integer of 6 to 10.

TABLE Ia

Components and rated properties of emulsion concentrate compositions of the present invention

| No | Toxicant* | Phenol | Surfactant A | amount | Surfactant B | amount | Solvent | amount | B | E | C |
|---|---|---|---|---|---|---|---|---|---|---|---|
| 1 | 62.9 | 15.0 | c | 7.0 | | | MCB; | 15.1 | S | S | U |
| 2 | 62.4 | 22.4 | c | 7.0 | | | MCB; | 8.2 | U | S | S |
| 3 | 62.4 | 20.4 | c | 7.0 | | | MCB; 8.2; and $N_3$ | 2.0 | U | S | S |
| 4 | 66.0 | 23.0 | c | 5.0 | | | m. ol. | 6.0 | S | S | U |
| 5 | 66.0 | 23.0 | c | 5.0 | | | $N_2$ | 6.0 | U | S | S |
| 6 | 62.4 | 23.4 | e | 5.0 | | | MCB; | 9.2 | U | S | S |
| 7 | 62.4 | 20.4 | e | 7.0 | | | MCB; 8.2; and $N_3$ | 2.0 | U | S | S |
| 8 | 65.0 | 19.0 | e | 7.0 | | | MCB; | 9.0 | U | S | S |
| 9 | 62.4 | 23.4 | j | 5.0 | | | MCB; | 9.2 | S | S | U |
| 10 | 65.0 | 19.0 | j | 7.0 | | | $N_2$; 4.6; and 3 NOX; | 4.4 | S | S | U |
| 11 | 65.3 | 17.0 | j | 7.0 | | | $N_2$; 6.0; and n. phen | 4.6 | S | S | U |
| 12 | 62.4 | 23.4 | a | 3.5 | b | 1.5 | MCB; | 9.2 | U | S | S |
| 13 | 65.2 | 23.0 | a | 3.5 | b | 1.5 | m. ol. | 6.8 | S | S | U |
| 14 | 60.0 | 20.0 | i | 3.5 | h | 1.5 | Xylene | 15.0 | U | S | S |

* No. 1–8 inclusive 97% pure; 9–14 inclusive 93% pure

Property Rating System
Properties
B(Bloom): S(atisfactory) if B is greater than 10%
E(Emulsion): S(atisfactory) if emulsion forms on agitation
C(crystallization): S(atisfactory) if sample stored at 25° F. shows no trace of crystallization: otherwise: U(nsatisfactory)

TABLE Ib

Components and rated properties of emulsion concentrate compositions of the present invention

| No | Toxicant* | Phenol | Surfactant A | amount | Surfactant B | amount | Solvent | amount | B | E | C |
|---|---|---|---|---|---|---|---|---|---|---|---|
| 15 | 64.5 | 23.2 | e | 4.7 | f | 4.7 | $N_2$ | 2.9 | — | — | 0 |
| 16 | 66.0 | 22.3 | e | 4.4 | f | 5.2 | $N_2$ | 2.9 | + | 0 | 0 |
| 17 | 66.0 | 22.5 | c | 5.2 | f | 5.2 | $N_2$ | 3.0 | + | 0 | 0 |
| 18 | 66.0 | 25.2 | c | 2.9 | f | 2.9 | $N_2$ | 2.9 | 0 | — | + |
| 19 | 66.0 | 26.4 | d | 4.6 | f | 1.1 | $N_2$ | 1.9 | — | — | + |
| 20 | 66.0 | 25.7 | d | 5.0 | f | 1.2 | $N_2$ | 2.1 | — — | — | + |
| 21 | 66.0 | 25.0 | d | 4.8 | f | 1.2 | $N_2$ | 3.0 | — — | — | + |
| 22 | 66.0 | 22.8 | d | 6.2 | f | 1.5 | $N_2$ | 3.5 | — | + | 0 |
| 23 | 66.0 | 24.5 | d | 5.9 | f | 1.5 | $N_2$ | 2.1 | — — | + | + |
| 24 | 66.0 | 23.0 | d | 6.4 | f | 1.6 | $N_2$ | 3.0 | — | ++ | 0 |
| 25 | 66.0 | 23.5 | d | 6.2 | f | 1.6 | $N_2$ | 2.7 | — | ++ | 0 |
| 26 | 66.0 | 22.5 | d | 6.4 | f | 1.6 | $N_2$ | 3.5 | — | + | 0 |
| 27 | 66.0 | 23.5 | d | 6.2 | f | 1.6 | $N_2$ | 2.7 | — | — | 0 |
| 28 | 66.0 | 20.7 | d | 7.4 | f | 1.8 | $N_2$ | 4.1 | + | ++ | — |
| 29 | 66.0 | 21.7 | d | 7.0 | f | 1.8 | $N_2$ | 3.5 | + | ++ | — |
| 30 | 66.0 | 22.3 | d | 6.6 | f | 2.2 | $N_2$ | 2.9 | + | + | 0 |

*93% pure

Property Rating System

| ** Properties | ++ | + | 0 | — | — — |
|---|---|---|---|---|---|
| B(Bloom) | >80% | 60–80% | 30–60% | 10–30% | <10% |
| E(Emulsion) | No cream | ≦1 ml | 1–2 ml | 2–4 ml | 4–5 ml |
| C(Crystallization) | 20° F./No | 20° F./Yes | 25° F./Yes | 30° F./Yes | 30° F./Yes |
| | | 25° F./No | 30° F./No | Reversible, 12 hrs. at room temp. | Not Reversible, 12 hrs. at room temperature |

EXAMPLE 2

Determination of the crystallization point of 2-chloro-N-isopropyl-2',3'-dimethylacetanilide in MCB in the presence of phenol Utilizing the procedure of Example 1, 2-chloro-N-isopropyl-2',3'-dmethylacetanilide and phenol are melted together and then mixed with monochlorobenzene (MCB). The temperatures at which the above compound crysallizes out of the MCB solution in the presence of phenol is determined. The results obtained, and the composition of the mixtures is summarized in Table II, hereinbelow, wherein it can be seen that as the molar ratio of herbicide to phenol is brought within that preferred in the present invention, the resistance of said compound to crystallization is increased.

TABLE II

Crystallization points of herbicide/phenol mixtures in MCB

| Composition in Weight % | | | Herbicide: Phenol | Crystallization |
|---|---|---|---|---|
| Herbicide | Phenol | MCB | (molar ratio) | Point °C. |
| 63.0 | 10.0 | 27.0 | 1:0.4 | 4.4 |
| 63.0 | 15.0 | 22.0 | 1:0.6 | −5.5 |
| 63.0 | 20.0 | 17.0 | 1:0.85 | −11.5 |
| 63.0 | 25.0 | 12.0 | 1:1.05 | −12 |

What is claimed is:

1. An emulsifiable liquid composition which comprises in admixture: 50% to 70% by weight of 2-chloro-N-isopropyl-2',3'-dimethylacetanilide, 23.5% to 30% by weight of phenol, with the proviso that the molar ratio of 2-chloro-N-isopropyl-2',3'-dimethylacetanilide to phenol be about 1:0.8 to 1:1.1, 2% to 15% by weight of a pair of surfactants in a 1:1 to 4:1 weight ratio, and wherein the first surfactant is a mixture of dodecylbenzene sulfonate and ethoxylated nonylphenol, and the second surfactant is a mixture of mono and diesters of orthophosphoric acid represented by the formulas:

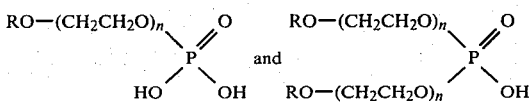

wherein R is $C_8$–$C_{20}$ alkyl or $C_8$–$C_{20}$ alkylphenyl and n is an integer of 6 to 10; and the composition is totaled to 100% with an inert aromatic solvent.

2. The composition according to claim 1, wherein the amount of 2-chloro-N-isopropyl-2',3'dimethylacetanilide is 64% to 66%, by weight, the amount of phenol is 23.5% to 30%, % by weight, the amount of the first surfactant is 2.5% to 7.5%, by weight, the amount of the second surfactant is 1% to 6%, by weight, and the composition is totaled to 100% with an inert aromatic solvent having a specific gravity at 15.56/15.56° C. of 0.853–0.875, a flash point TCC min °C. of 37.8, a Kauri-Butanol value, min 92, an aromatics Vol. %, min. 95, and a boiling point range °C. of 143–171.

3. The composition of claim 1 or claim 2 wherein the molar ratio of the 2-chloro-N-isopropyl-2',3'-dimethylacetanilide to the phenol is about 1:0.85 to 1:1.05.

4. The composition according to claim 2 comprising in admixture: 66% of 2-chloro-N-isopropyl-2',3'-dimethylacetatnilide, 23.5% by weight of phenol, 6.2% by weight of the said first surfactant, 1.6% by weight of the said second surfactant and 2.7% by weight of said inert aromatic solvent.

* * * * *